(12) United States Patent
Bianco et al.

(10) Patent No.: US 7,078,176 B2
(45) Date of Patent: Jul. 18, 2006

(54) DETECTION AND QUANTIFICATION OF CRIPTO-1

(75) Inventors: Caterina Bianco, Bethesda, MD (US); David Salomon, Germantown, MD (US)

(73) Assignee: The United States of America as represented by the Department of Health and Human Serivices, Washington, DC (US)

( * ) Notice: Subject to any disclaimer, the term of this patent is extended or adjusted under 35 U.S.C. 154(b) by 208 days.

(21) Appl. No.: 10/470,322

(22) PCT Filed: Jan. 23, 2002

(86) PCT No.: PCT/US02/02225

§ 371 (c)(1),
(2), (4) Date: Jul. 25, 2003

(87) PCT Pub. No.: WO02/059620

PCT Pub. Date: Aug. 1, 2002

(65) Prior Publication Data

US 2004/0077025 A1    Apr. 22, 2004

Related U.S. Application Data

(60) Provisional application No. 60/264,643, filed on Jan. 26, 2001.

(51) Int. Cl.
*G01N 33/53*    (2006.01)
(52) U.S. Cl. .................. 435/7.1; 435/7.92; 435/7.93; 435/7.94; 436/164; 436/518
(58) Field of Classification Search ............... 435/7.1, 435/7.92–7.95; 436/501, 518, 524, 164, 436/172
See application file for complete search history.

(56) References Cited

U.S. PATENT DOCUMENTS

| | | | |
|---|---|---|---|
| 5,256,643 A | 10/1993 | Persico et al. | |
| 5,264,557 A | 11/1993 | Salomon et al. | |
| 5,620,866 A | 4/1997 | Salomon et al. | |
| 5,650,285 A | 7/1997 | Salomon et al. | |
| 5,654,140 A | 8/1997 | Persico et al. | |
| 5,792,616 A | 8/1998 | Persico et al. | |
| 5,854,399 A | 12/1998 | Salomon et al. | |
| 5,968,839 A * | 10/1999 | Blatt et al. ................. | 436/513 |
| 5,981,215 A * | 11/1999 | Meissner et al. .......... | 435/69.1 |
| 6,777,198 B1 * | 8/2004 | Mendel-Hartvig et al. . | 435/7.94 |

OTHER PUBLICATIONS

Salomon et al., The EGF-CFC family: novel epidermal growth factor-related proteins in development and cancer, Endocrine-Related Cancer (Dec. 2000), 7 199-226.*

Bianco et al., Cripto-1 in Human Milk, Proceeding of the American Association for Cancer Research, vol. 41, Mar. 2000, p. 786.*
Abe et al., *Digestive Diseases and Sciences*, 42(6), 1199-1209 (Jun. 1997).
Bianco et al., *J. Biol. Chem.*, 274, 8624-8629 (1999).
Bianco et al, *Breast Cancer Research and Treatment*, 66, 1-7 (2001).
Brandt et al., *J. Biol. Chem.*, 269 (25), 17320-17328 (1994).
Bryan et al., *Pediatr. Res.*, 45, 858-859 (1999).
Byrne et al., *J. of Pathology*, 185, 108-111 (1998).
Calhoun et al., *Pediatr.*, 105, e7 (2000).
Carpenter, *Science*, 210, 198-199 (1980).
Ciardiello et al., *Cancer Research*, 51, 1051-1054 (Feb. 1, 1991).
Ciardiello et al., *Proc. Natl. Acad. Sci. U.S.A.*, 88, 7792-7796 (1991).
Ciccodicola et al., *EMBO J.*, 8(7), 1987-1991 (1989) (Abstract).
DeLuca et al., *Int. J. Cancer*, 80, 589-594 (1999).
DeSantis et al., *Cell Growth & Differentiation*, 8, 1257-1266 (Dec. 1997).
DeSantis et al., *Cell Death and Differentiation*, 7, 189-196 (2000).
Ding et al., *Nature*, 395, 702-707 (1998).
Dono et al., *Develop.*, 118, 1157-1168 (1993).
Donnet-Hughes et al., *Immunol. Cell. Biol.*, 78, 74-79 (2000).
Dirix et al., *Br. J. Cancer*, 76, 238-243 (1997).
Dublin et al., *Int. J. Oncol.*, 7, 617-622 (1995).
Dunbar et al., *Biochem. J.*, 344, 713-721 (1999).
Friess et al., *Int. J. Cancer*, 56, 668-674 (1994).
Fujii et al., *J. Pathol.*, 180, 166-168 (1996).
Gritsman et al., *Cell*, 97, 121-132 (1999).
Grosvenor et al., *Endocrin. Rev.* 14, 710-728 (1992).
Hawkes et al., *Pediatr. Res.*, 46, 194-199 (1999).
Herrington et al., *J. Cell Physiol.*, 170, 47-56 (1997).
Kannan et al., *J. Biol. Chem.*, 272, 3330-3335 (1997).
Kenney et al., *Mol. Reprod. Develop.*, 41, 277-286 (1995).
Kenney et al., *Mol. Carcinogenesis*, 15, 44-56 (1996).
Kidwell et al., In Atkinson and Lonnerdal (eds.), *Protein and Non-Protein Nitrogen in Human Milk*, 78-91, CRC Press, Boca Raton, FL, (1989).
Kinoshita et al., *Cell*, 83, 621-630 (1995).

(Continued)

*Primary Examiner*—Long V. Le
*Assistant Examiner*—Gary W. Counts
(74) *Attorney, Agent, or Firm*—Leydig, Voit & Mayer, Ltd.

(57) ABSTRACT

The present invention provides methods and compositions for the detection and quantification of Cripto-1. In particular, the present invention provides methods and compositions for the detection and quantification of Cripto-1 in samples such as milk, plasma, serum, and other biological fluids. In particularly preferred embodiments, the present invention finds use in the detection and/or quantification of Cripto-1 in human milk, plasma, serum, and other biological fluids.

25 Claims, 6 Drawing Sheets

OTHER PUBLICATIONS

Minchiotti et al., *Mech. Develop.*, 90, 133-142 (2000).
Niemeyer et al., *Cell Death Different.* 5, 440-449 (1998).
Niemeyer et al., *Int. J. Cancer*, 81, 588-591 (1999).
Normanno et al. *Breast Cancer Res. Treatment*, 29, 11-27 (1994).
Okada et al., *Life Sci.*, 48, 1151-1156 (1991).
Okajima et al., *Cancer Lett.*, 111, 67-70 (1997).
Panico et al., *Int. J. Cancer*, 65, 51-56 (1996).
Qi et al., *Br. J. Cancer*, 69, 903-910 (1994).
Read et al., *Pediatr. Res.*, 18, 133-139 (1984).
Rodriguez-Palmero et al., *Clin. Perinatol*, 26, 335-359 (1999).
Salomon et al., *Crit. Rev. Oncol. Hematol.*, 19, 183-232 (1995).
Salomon et al., *BioEssays*, 21, 61-70 (1999).
Schams, *Endocrin. Regul.*, 28, 3-8, (1994).
Seno et al, *Growth Factors*, 15, 215-229 (1998).
Shen et al., *Develop.*, 124, 429-442 (1997).
Siafakas et al., *Pediatr. Res.*, 45, 652-657 (1999).
Snedecker et al., *Proc. Natl. Acad. Sci. U.S.A.*, 88, 276-280 (1991).
Starkey et al., *J. Clin. Endocrinol. Metab.*, 45, 1144-1153 (1977).
Taniguchi et al., *Clin. Cancer Res.*, 1, 1031-1034 (1995).
Yamada et al., *Am. J. Reprod. Immunol.*, 40, 112-120 (1998).
Zhang et al., *Cell*, 92, 241-251 (1998).
Zhang et al. *Anticancer Res.*, 19, 1427-1432 (1999).

* cited by examiner

A

31.7 kDa -
18.5 kDa -

1 2 3 4 5 6 7 8 9

B

31.7 kDa -
18.5 kDa -

10 11 12 13 14 15 16 17 18

C

31.7 kDa -
18.5 kDa -

19 20 21 22 23 24

DETECTION AND QUANTIFICATION OF CRIPTO-1

FIELD OF THE INVENTION

The present invention provides methods and compositions for the detection and quantification of Cripto-1. In particular, the present invention provides methods and compositions for the detection and quantification of Cripto-1 in samples such as milk, plasma, serum, and other biological fluids.

BACKGROUND OF THE INVENTION

Human Cripto-1 (CR-1) is a member of a larger family of structurally related proteins, namely the EGF-CFC family that includes mouse CR-1, mouse cryptic, *Xenopus* FRL-1, and zebrafish one-eyed pinhead (oep) (Ciccodicola et al., EMBO J., 8:1987–1991 [1090]; Dono et al., Develop., 118:1157–1168 [1993]; Shen et al., Develop., 124:429–442 [1997]; Kinoshita et al., Cell 83:621–630 [1995]; and Zhang et al., Cell 92:241–251 [1997]). These proteins are characterized by the presence of a modified EGF-like domain and by a second cysteine-rich region called CFC domain (Salomon et al., BioEssays 21:61–70 [1999]). They also share a conventional signal sequence and a hydrophobic C-terminus that is essential for membrane-anchorage by a glycosylphosphatidylinositol (GPI) moiety (Minchiotti et al., Mech. Develop., 90:133–142 [2000]). The human CR-1 and mouse CR-1 genes encode glycoproteins of 188 and 171 amino acids respectively, with molecular weights of 28 and 24 kDa, resepectively (Brandt etal., J. Biol. Chem., 269: 17320–17328 [1994]). The EGF-CFC proteins perform an essential role during early vertebrate embryogenesis by promoting mesoderm formation and cell migration during gastrulation (Zhang et al., supra; Gritsman et al., Cell 97:121–132 [1999]; and Ding et al., Nature 395:702–707 [1998]). CR-1 mRNA and immunoreactive protein are expressed in several human breast cancer cell lines, in approximately 80% of human primary breast carcinomas, and in mammary tumors that arise in mice that overexpress different transgenes in the mammary gland such as c-neu, transforming growth factor α (TGFα), ini-3, polyoma middle T gene, and SV-40 large T gene (Kenney et al., Mol. Carcinogen., 15:44–56 [1996]; Qi et al., Brit. J. Cancer 69:903–910 [1994]; and Dublin et al., Int. J. Oncol., 7:617–622 [1995]). CR-1 can also be detected in the developing mouse mammary gland with different levels of expression in the virgin, pregnant, lactating and aged mammary gland (Kenney et al., Mol. Reprod. Develop., 41: 277–286 [1995]). In the virgin mammary gland, CR-1 expression is found primarily in the cap stem cells of the growing terminal end buds and CR-1 expression increases several fold in ductal epithelial cells during pregnancy, lactation, and in the aged mammary gland (Kenney et al., Mol. Reprod. Develop., 41:277–286 [1995]; and Herrington et al., J. Cell. Physiol., 131:215–226 [1997]). In addition, CR-1 can modulate the expression of milk proteins in a mouse mammary epithelial cell line (HC-11) and in primary mouse mammary explant cultures (De Santis et al., Cell Growth Different., 8:1257–1266 [1997]). However, despite the identification of CR-1 in mammary glands, its role in mammary health and disease has remained largely unknown. Thus, there remains a need in the art for methods that provide for simple detection and quantitation of Cripto-1 in various biological fluids.

SUMMARY OF THE INVENTION

The present invention provides methods and compositions for the detection and quantification of Cripto-1. In particular, the present invention provides methods and compositions for the detection and quantification of Cripto-1 in samples such as milk (e.g., human milk) and other biological fluids.

The present invention provides methods for the detection of Cripto-1, comprising: providing a fluid sample suspected of containing Cripto-1, and an antibody directed against Cripto-1; exposing the fluid sample to the antibody under conditions such that the Cripto-1 and antibody bind to form an antigen-antibody complex; and detecting the antigen-antibody complex. In some preferred embodiments, the fluid sample is selected from the group consisting of milk, serum, and plasma. In still particularly preferred embodiments, the fluid sample is from a human. In further embodiments, the antibody is selected from the group consisting of monoclonal antibodies and polyclonal antibodies. In alternative preferred embodiments the method is an enzyme-linked immunosorbent assay method. In still further embodiments, the method further comprises the step of quantitating the amount of Cripto-1 in the fluid sample.

The present invention also provides methods for quantitating Cripto-1 in a fluid sample, comprising: providing a fluid sample containing Cripto-1, and an antibody directed against Cripto-1; exposing the fluid sample to the antibody under conditions such that the Cripto-1 and antibody bind to form an antigen-antibody complex; and measuring the amount of antigen-antibody complex. In some preferred embodiments, the fluid sample is selected from the group consisting of milk, serum, and plasma. In some particularly preferred embodiments, the fluid sample is from a human. In further embodiments, the antibody is selected from the group consisting of monoclonal antibodies and polyclonal antibodies. In alternative preferred embodiments the method is an enzyme-linked immunosorbent assay method. In still further embodiments, the method further comprises the step of quantitating the amount of Cripto-1 in said fluid sample.

The present invention also provides methods for detecting and quantitating Cripto-1 in a sample, comprising: providing a fluid sample suspected of containing Cripto-1, and an antibody directed against said Cripto-1; exposing the fluid sample to the antibody under conditions such that the Cripto-1 and antibody bind to form an antigen-antibody complex; detecting the antigen-antibody complex; and measuring the amount of the antigen-antibody complex. In some preferred embodiments, the fluid sample is selected from the group consisting of milk, serum, and plasma. In some particularly preferred embodiments, the fluid sample is from a human. In further embodiments, the antibody is selected from the group consisting of monoclonal antibodies and polyclonal antibodies. In alternative preferred embodiments the method is an enzyme-linked immunosorbent assay method.

DESCRIPTION OF THE INVENTION

Figure 1:
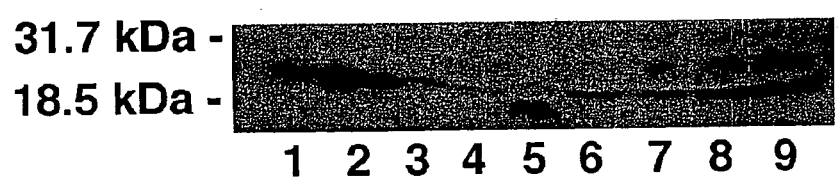
FIGS. 1A–C provide results of Western blot analysis of CR-1 in 24 human milk samples (run on a 4–14% SDS-PAGE gel) and probed with an anti-CR-1 rabbit polyclonal antibody.
Figure 1:
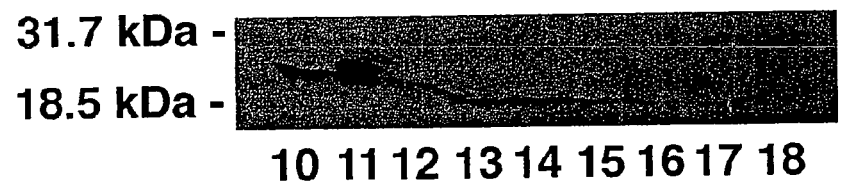
Figure 1:

The present invention provides methods and compositions for the detection and quantification of Cripto-1. In particular, the present invention provides methods and compositions for the detection and quantification of Cripto-1 in samples such as milk, serum, plasma, and other biological fluids.

In addition to containing nutrients, vitamins and minerals, human milk also is composed of a variety of growth factors and cytokines that are thought to be important in the regulation of growth and secretory function of the mammary gland and in the regulation of growth, development and maturation of the intestinal mucosa and immune system in the newborn (Kidwell et al., In Atkinson and Lonnerdal (eds), *Protein and Non-Protein Nitrogen in Human Milk*, CRC Press, Boca Raton, Fla. [1989], pp. 77–91). Among the several growth factors identified in human milk, EGF and TGFα are the most important mitogenic factors for normal mammary epithelium (Carpenter, Science 210:198–199 [1980]; and Okada et al., Life Sci., 48:1540–1543 [1991]). In this respect, several studies have demonstrated that both EGF and TGFα stimulate the proliferation of human and mouse mammary epithelial cells and it is contemplated that their presence in human milk is physiologically important for mammary epithelial cell growth and differentiation (Snedecker et al., Proc. Natl. Acad. Sci USA 88:1063–1069 [1991]).

Indeed, human milk contains a variety of different proteins and peptides that possess biological activity (Rodriguez-Palmero et al., Clin. Perinatol., 26:355–359 [1999]). Among the many bioactive substances present in milk, are a large number of growth factors and cytokines (Grosvenor et al., Endocrin. Rev., 14:710–728 [1992]). These include insulin, insulin-like growth factor 1 (IGF-1), EGF, TGFα, transforming growth factor β 1 (TGF-β 1) and TGF-β 2, bombesin, mammary-derived growth factor I and II, colony stimulating factor, human milk growth factor I, II and III, platelet derived growth factor, hepatocyte growth factor, vascular endothelial cell growth factor, betacellulin, granulocyte colony-stimulating factor (GSF), tumor necrosis factor α (TNFα), interleukin-1 (IL-1), and interleukin-6 (IL-6) (Grosvenor et al., Endocrin. Rev., 14:710–728 [1992]; Scahms, Endocrin. Regul., 28:3–8 [1994]; Yamada et al., Am. J. Reprod. Immunol., 40:112–120 [1998]; Bryan et al., Pediatr. Res., 45:858–859 [1999]; Siafakas et al., Pediatr. Res., 45:652–657 [1999]; Hawkes et al., Pediatr. Res., 46:194–199 [1999]; Donnet-Hughes et al., Immunol. Cell Biol., 78:74–79 [2000]; Calhoun et al., Pediatr., 105:1–6 [2000]; and Dunbar et al., Biochem. J., 344:713–721 [1999]).

Experiments conducted during the development of the present invention demonstrated for the first time that a member of the EGF-CFC family of peptides, CR-1, is present in human milk. As described herein, twenty four human milk samples were analyzed for the presence of CR-1 using Western blot analysis and ELISA. CR-1 protein was identified in all the samples with concentrations between 62 and 118 ng/ml. Similar concentrations have been reported for EGF in human milk (Carpenter, Science 210:198–199 [1980]; and Okada et al., Life Sci., 48:1540–1543 [1991]). Unfortunately, no information was available about the time when the milk samples were collected after delivery; therefore, it was not possible to ascertain if a potential correlation might exist between the CR-1 concentration in human milk and a defined period of lactation. In this respect, several growth factors reach their highest concentrations in the colostrum, fall rapidly in the postpartum and remain constant until the end of lactation (Yamada et al., Am. J. Reprod. Immunol., 40:112–120 [1998]; Bryan et al., Pediatr. Res., 45:858–859 [1999]; and Read et al., Pediatr. Res., 18:133–139 [1984]). CR-1 that was purified from human milk by immunoaffinity chromatography was different in size from the human recombinant CR-1 protein, as assessed by Western blot analysis. In this respect, human CR-1 protein contains a single N-glycosylation site, five potential myristylation sites and three consensus sites for potential phosphorylation by protein kinase A and protein kinase C (Brandt et al., J. Biol. Chem., 269:17320–17328 [1994]). In fact, in addition to native human and mouse CR-1 proteins of 28 and 24 kDa in size, other proteins ranging from 14 to 60 kDa which are immunologically related to mouse CR-1 have been described (Kenney et al., Mol. Carcinogen., 15:44–56 [1996]; and Seno et al., Growth Factors 15:215–229 [1997]). It is contemplated that these postranslational modifications account for the difference in mobility of milk-derived CR-1 versus human recombinant CR-1 protein. However, an understanding of the mechanism(s) involved is not necessary in order to use the present invention. Finally, milk-derived CR-1 protein is biologically active since it was able to stimulate MAPK phosphorylation in NMuMG mouse mammary epithelial cells. The activation of MAPK pathway is mediated by the binding of CR-1 to a still unknown cell surface receptor (Bianco et al., J. Biol. Chem., 274:8624–8629 [1999]).

It is contemplated that the presence of biologically active CR-1 in milk is physiologically significant, based upon some of the biological effects of this growth factor. For example, besides producing a mitogenic effect in mouse mammary epithelial cells through the activation of the ras/ra MAPK pathway (Kannan et al., J. Biol. Chem., 272:3330–3335 [1997]), CR-1 can also modulate the differentiation of a mouse mammary epithelial cell line (HC-11) and primary mouse mammary explant cultures established from midpregnant mice (De Santis et al., Cell Growth Different., 8:1257–1266 [1997]). HC-11 cells and primary mouse mammary epithelial cells respond to the lactogenic hormones dexamethasone, insulin and prolactin (DIP) by expressing milk proteins such as β-casein and whey acidic protein (WAP). CR-1 is an inhibitor of β-casein and WAP expression in confluent HC-11 cells and in static primary mouse mammary explant cultures in response to lactogenic hormones. However, in logarithmically growing HC-11 cells, CR-1 can sensitize cells to subsequent lactogenic hormone-induced increase in β-casein expression (De Santis et al., Cell Growth Different., 8:1257–1266 [1997]). The inhibitory effect of CR-1 on β-casein expression in response to DIP in HC-11 cells is mediated through the activation $p21^{ras}$-and phosphatidylinositol 3'-kinase-dependent pathway. Therefore, CR-1 has either a mitogenic or differentiation effect on mouse mammary epithelial cells depending on the signal transduction pathway that is activated. Thus, it is contemplated that CR-1 in human milk modulates two different responses. During pregnancy when CR-1 expression is elevated (Kenney et al., Mol. Reprod. Develop., 41:277–286 [1995]; and Herrington et al., J. Cell Physiol., 131:215–226 [1997]), it is contemplated that CR-1 exerts its mitogenic effect on the mammary epithelium, thereby stimulating proliferation and differentiation of mammary epithelial cells with the induction of milk protein expression. In contrast, during lactation when cell proliferation has ceased, it is contemplated that CR-1 present in milk is important in reducing milk protein expression and therefore inhibiting differentiation and facilitating involution of the mammary gland. Indeed, this function is supported by the recent demonstration that CR-1 can induce apoptosis in confluent, survival-factor depleted HC-11 cells (De Santis et al., Cell Death Different., 7:189–196 [2000]). This effect is mediated through an increase in the expression of a caspase-3-like protease and a downregulation in the level of $Bcl-x_1$ (De Santis et al., Cell Death Different., 7:189–196 [2000]). However, an understanding of the mechanism(s) is not necessary in order to use the present invention. Indeed, it is not intended that the present invention be limited to any particular mechanism(s).

In addition to regulating mouse mammary gland growth and morphogenesis, it has been demonstrated that CR-1 may be relevant in the pathogenesis of human breast cancer (Qi et al., Brit. J. Cancer 69:903–910 [1994]; Dublin et al., Int. J. Oncol., 7:617–622 [1995]; and Salomon et al., Crit. Rev. Oncol. Hematol, 19:183–232 [1995]). CR-1 expression has been detected in approximately 80% of infiltrating ductal or lobular carcinomas and in 50% of ductal carcinoma in situ (Qi et al., Brit. J. Cancer 69:903–910 [1994]. Interestingly, only 15% of non-involved adjacent mammary epithelium specimens were positive for CR-1 expression, indicating a role for CR-1 as potential tumor marker for this disease (Qi et al., Brit. J. Cancer 69:903–910 [1994]). However, no significant correlations were found between CR-1 expression and various clinicopathological parameters, such as tumor size, lymph node involvement, proliferative index or estrogen and progesterone receptor status (Dublin et al., Int. J. Oncol., 7:617–622 [1995]). The data included herein, which demonstrate the presence of CR-1 in human milk, indicates that CR-1 expressed at sufficiently high enough levels by breast tumors is released by cancer cells and reaches the blood circulation. Therefore, it is contemplated that detection and measurement of CR-1 levels in human serum and/or plasma will find clinical significance in the diagnosis of breast cancer. In fact, several different growth factors and cytokines have been reported to be present in the plasma or serum of human breast cancer patients and their concentrations are significantly correlated with disease progression and response to chemotherapy and endocrine therapy (Zhang et al., Anticancer Res., 19:1427–1432 [1999]; Taniguchi et al., Clin. Cancer Res., 1:1031–1034 [1995]; and Dorix et al., Br. J. Cancer 76:238–243 [1997]). Indeed, experiments were conducted during the development of the present invention to detect CR-1 in human plasma of breast cancer patients.

During the development of the present invention, an evaluation was conducted to determine whether the increase in CR-1 expression that is detected in the mouse mammary gland during pregnancy and lactation is associated with the secretion of this growth factor into milk. Based on these early results, the present invention, which provides ELISA and Western blot analysis methods suitable for the detection and quantification of CR-1 in human milk and other samples was developed. As indicated herein, the methods and compositions provide the means to detect a specific band for CR-1 of 28 kDa in milk samples with concentrations between 62 and 118 ng/ml. In addition, as discussed in greater detail herein, CR-1 purified from human milk using an immunoaffinity column, was able to stimulate the phosphorylation of MAPK in NMuMG mouse mammary epithelial cells.

Twenty four samples of human milk were analyzed for CR-1 expression by Western blot analysis using a monospecific rabbit polyclonal anti-CR-1 antibody. A band of 28 kDa that reacted with the rabbit polyclonal anti-CR-1 antibody was identified at varying intensity in the human milk samples (See, FIG. 1). All the samples expressed immunoreactive CR-1 protein but to various degrees.

Figure 2:
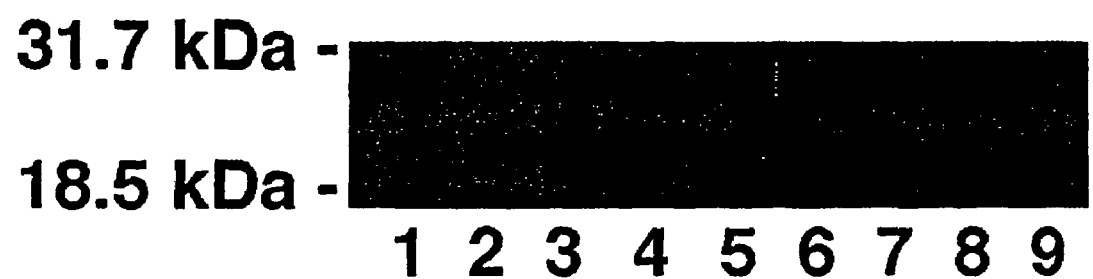
FIG. 2 shows a Western blot analysis of CR-1 in human milk using polyclonal anti-CR-1 antibody that was pre-incubated with recombinant CR-1. Human milk samples 1–9 were run on a 4–20% SDS-PAGE gel and probed with 1:1000 dilution of rabbit polyclonal anti-CR-1 antibody that had been preincubated with recombinant CR-1 protein (1 µg/ml) for 2 hours at room temperature.
Figure 3:
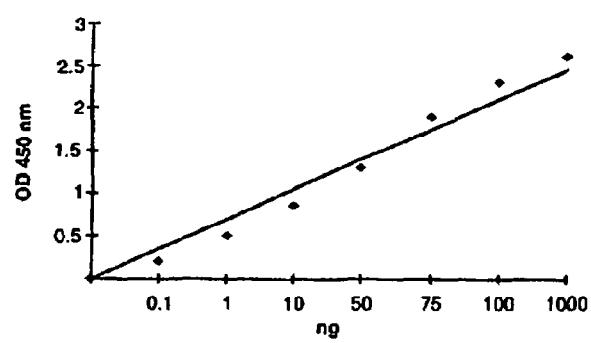
FIG. 3 provides ELISA results for detection of CR-1 in human milk samples. In these assays, 96 microtiter wells were coated overnight with 200 µl delipidated human milk samples and blocked with 2% milk. Panel A provides results showing the concentration of CR-1 in the samples was estimated using different concentrations of recombinant CR-1 protein. Panel B provides results for plates incubated with rabbit polyclonal anti-CR-1 antibody.
Figure 3:
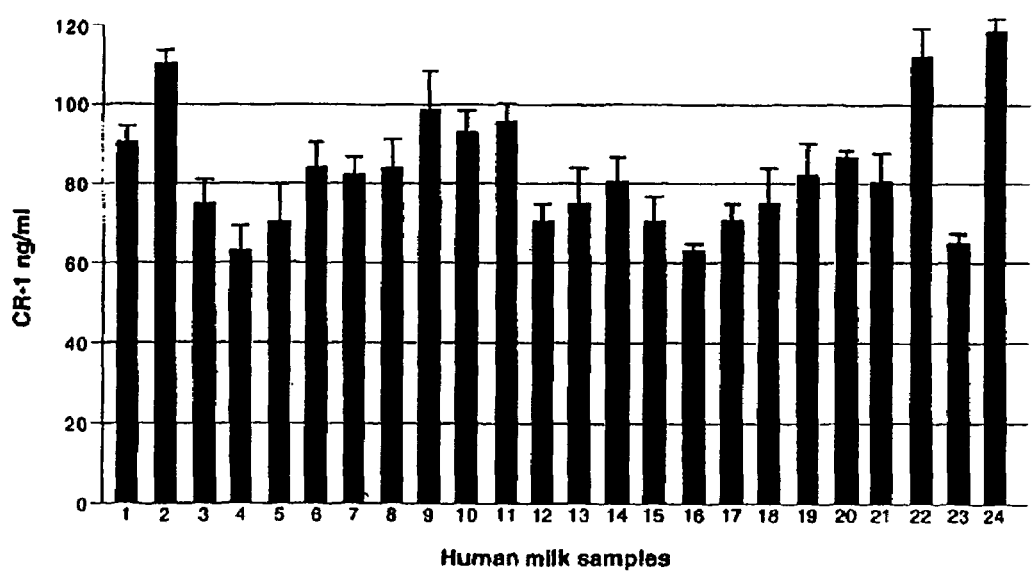

To demonstrate that the band recognized by the anti-CR-1 antibody is specific, samples 1 to 9 were probed with the rabbit polyclonal anti-CR-1 antibody that had been preincubated with an excess of recombinant CR-1. No bands were detected when the samples were incubated with the anti CR-1 antibody preabsorbed with the CR-1 protein, demonstrating the specificity of the band that was recognized by the anti-CR-1 antibody (FIG. 2). The presence and amount of CR-1 in human milk was also assessed and quantified by ELISA. Using the recombinant CR-1 protein as a standard at different concentrations, the concentration of CR-1 in the delipidated human milk samples was estimated. FIG. 3, Panel A shows that the rabbit anti-CR-1 polyclonal antibody can linearly detect recombinant human CR-1 over a concentration range of 100 pg to 1 μg. Immunoreactive CR-1 was present at concentrations from 62 to 118 ng/ml in the milk samples (See, FIG. 3, Panel B). There was a significant correlation between the relative amounts of the 28 kDa CR-1 immunoreactive protein in the milk samples as detected by Western blot analysis and the concentration of immunoreactive CR-1 that was measured in the ELISA.

To evaluate whether CR-1 in human milk is biologically active on mammary epithelial cells, a single human milk sample with high levels of CR-1 expression as determined by Western blot analysis and ELISA (sample number 2) was chosen for purification. CR-1 was purified from delipidated human milk using an immunoaffinity column to which the anti-CR-1 rabbit polyclonal antibody was bound. After concentration, dialysis and estimation of the concentration of CR-1 as determined by Western blot analysis (FIG. 4), the purified CR-1 protein was assayed for its activity on NMuMG mouse mammary epithelial cells.

It has previously been demonstrated in several mouse and human mammary epithelial cell lines that CR-1 can induce a rapid increase in the tyrosine phosphorylation of p66, p52 and p46 isoforms of Shc which can than subsequently activate a ras/raf/MAPK pathway as evidenced by the enhanced phosphorylation of p42 and p44 isoforms of MAPK (Kannan et al., J. Biol. Chem., 272:3330–3335 [1997]). NMuMG mouse mammary epithelial cells respond to recombinant or chemically synthesized CR-1 with an increase in the phosphorylation of Shc and MAPK (Seno et al., Growth Factors 15:215–229 [1998]; and Kannan et al., supra). To ascertain whether CR-1 purified from human milk had comparable activity to recombinant CR-1, serum-starved NMuMG cells were treated with different concentrations of the immunopurified milk-derived CR-1 protein and compared to recombinant human CR-1. A dose-dependent activation of MAPK was detected following treatment of the cells with milk-derived CR-1 (See, FIG. 5). Recombinant human CR-1 (100 ng/ml) was also able to stimulate MAPK phosphorylation which was nearly equivalent to the level of MAPK stimulation by 100 ng/ml of milk-derived CR-1.

Definitions

The terms "sample" and "specimen" in the present specification and claims are used in their broadest sense. In preferred embodiments, these terms encompass all types of samples obtained from humans and other animals, including but not limited to, body fluids such as urine, blood, cerebrospinal fluid (CSF), fecal matter, semen, and saliva. However, biological samples may be animal, including human, fluid or tissue, as these examples are not to be construed as limiting the sample types applicable to the present invention.

As used herein, the term "fluid sample" refers to a sample that is liquid. For example, the term encompasses bodily fluids (e.g., "biological fluids"), such as milk, blood, serum, plasma, CSF, urine, semen, saliva, serous fluid, etc. It is not intended that the present invention be limited to any particular fluid.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen or portion of an antigen.

As used herein, the terms "antigen fragment" and "portion of an antigen" are used in reference to a piece of an antigen. Antigen fragments or portions may occur in various sizes, ranging from a small percentage of the entire antigen to a large percentage, but not 100% of the antigen. However, in situations where "at least a portion of an antigen" is specified, it is contemplated that the entire antigen may be present. In some preferred embodiments, antigen fragments or portions comprise an "epitope" (e.g., an "antigenic determinant") recognized by an antibody. In other embodiments, antigen fragments or portions are be immunogenic (i.e., such fragments or portions are capable of inducing an immune response), while in other embodiments, the antigen fragments or portions are not immunogenic (i.e., such fragments or portions are not capable of inducing an immune response).

As used herein, the term "immunoassay" is used in reference to any method in which antibodies are used in the detection of an antigen. It is contemplated that a range of immunoassay formats be encompassed by this definition, including but not limited to direct immunoassays, indirect immunoassays, and "sandwich" immunoassays." A particularly preferred format is an enzyme-linked immunosorbent assay (ELISA). However, it is not intended that the present invention be limited to this format. It is contemplated that other formats, including radioimmunoassays (RIA), immunofluorescent assays (IFA), and other assay formats, including, but not limited to, variations on the ELISA method will find use in the method of the present invention. Indeed, it is contemplated that other antigen-antibody reaction formats will find use in the present invention, including but not limited to "flocculation" (i.e., a colloidal suspension produced upon the formation of antigen-antibody complexes), "agglutination" (i.e., clumping of cells or other substances upon exposure to antibody), "particle agglutination" (i.e., clumping of particles coated with antigen in the presence of antibody or the clumping of particles coated with antibody in the presence of antigen), "complement fixation" (i.e., the use of complement in an antibody-antigen reaction method), and other methods commonly used in serology, immunology, immunocytochemistry, histochemistry, and related fields.

As used herein, the term "cell staining" is used in reference to methods used to label or stain cells to enhance their visualization. This staining or labelling is achieved through the use of various compounds, including but not limited to, fluorochromes, enzymes, gold, and iodine. It is contemplated that the definition encompasses such methods as "in situ chromogenic assays," in which a test (i.e., an assay) is conducted on a sample in situ. It is also contemplated that the in situ chromogenic assay will involve the use of an immunoassay (i.e., an ELISA) or immunocytohistochemistry. However, it is not intended that the present invention be limited to any particular assay format for cell staining.

As used herein, the term "capture antibody" refers to an antibody that is used to bind an antigen and thereby permit the recognition of the antigen by a subsequently applied antibody. For example, in some preferred embodiments, the capture antibody is bound to a microtiter well and serves to bind antigens (e.g., Cripto-1) present in a sample added to the well. Another antibody (termed the "primary antibody") is then used to bind to the antigen-antibody complex, in effect to form a "sandwich" comprised of antibody-antigen-antibody. Detection of this complex can be performed by several methods. In some particularly preferred embodiments, the primary antibody is prepared with a label such as biotin, an enzyme, a fluorescent marker, or radioactivity, and is detected directly using this label. Alternatively, a labelled "secondary antibody" or "reporter antibody" which recognizes the primary antibody is added, forming a complex comprised of antibody-antigen-antibody-antibody. Again, appropriate reporter reagents are then added to detect the labelled antibody. In other embodiments, any number of additional antibodies are added as desired. In some embodiments, these antibodies are also be labelled with a marker, including, but not limited to an enzyme, fluorescent marker, or radioactivity.

As used herein, the term "reporter reagent" or "reporter molecule" is used in reference to compounds which are capable of detecting the presence of antibody bound to antigen. For example, in preferred embodiments, a reporter reagent is a calorimetric substance which is attached to an enzymatic substrate. Upon binding of antibody and antigen, the enzyme acts on its substrate and causes the production of a color. Other reporter reagents include, but are not limited to fluorogenic, chromogenic, luminogenic, and radioactive compounds or molecules. This definition also encompasses the use of biotin and avidin-based compounds (e.g., including compounds but not limited to neutravidin and streptavidin) as part of the detection system. In one embodiment of the present invention, biotinylated antibodies are used in conjunction with avidin-coated solid support.

As used herein the term "signal" is used in reference to an indicator that a reaction has occurred, for example, binding of antibody to antigen. It is contemplated that signals in the form of radioactivity, fluorogenic reactions, and enzymatic reactions will be used with the present invention. However, it is not intended that the present invention be limited to any particular signal. In some embodiments, the signal is assessed quantitatively and/or qualitatively.

As used herein, the term "amplifier" is used in reference to a system which enhances the signal in a test method such as an ELISA. However, it is not intended that the present invention be limited to the use of amplifiers in any particular assays system or format.

As used herein, the term "solid support" is used in reference to any solid material suitable for the attachment of various reagents such as antibodies, antigens, and/or other compounds. For example, in the ELISA method, wells of microtiter plates often provide solid supports. Other examples of solid supports include microscope slides, coverslips, beads, particles, cell culture flasks, as well as many other items.

As used herein, the term "kit" is used in reference to a combination of reagents and other materials. In preferred embodiments, the kits of the present invention comprise microtiter plates, buffers, labelled antibodies, positive and negative controls, instruction manuals for users, etc. It is not intended that the kits of the present invention be limited to any particular components, reagents, etc. Indeed, it is intended that various kit formats will find use with the present invention.

Experimental

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl)aminomethane); w/v (weight to volume); v/v (volume to volume); Amersham (Amersham Pharmacia Biotech, Arlington Heights, Ill.); Pierce (Pierce Chemical Co., Rockford, Ill.); ICN (ICN Pharmaceuticals, Inc., Costa Mesa, Calif.); Amicon (Amicon, Inc., Beverly, Mass.); ATCC (American Type Culture Collection, Rockville, Md.); Kirkergaard & Perry (Kirkergaard & Perry Laboratories, Gaithersburg, Md.); BioRad (BioRad, Richmond, Calif.); GIBCO BRL or Gibco BRL (Life Technologies, Inc., Gaithersburg, Md.); New England Biolabs (New England Biolabs, Inc., Beverly, Mass.); Pharmacia (Pharmacia, Inc., Piscataway, N.J.); and Sigma (Sigma Chemical Co., St. Louis, Mo.).

In these experiments, the human milk samples used were obtained from 24 healthy women. Data regarding the time when these samples were collected after delivery were not available. The samples were centrifuged at 14,000 rpm for 10 min and the aqueous layer of the milk was collected after removing the lipid layer.

NMuMG normal mouse mammary epithelial cells were cultured in Dulbecco's modified Eagle's medium containing 10% fetal bovine serum. Recombinant human CR-1 (rhCR-1) protein was expressed in E. coli and purified as known in the art (See, Seno et al., Growth Factors 15:215–229 [1998]).

EXAMPLE 1

Western Blot Analysis

In these experiments, 40 μl of delipidated human milk samples were loaded on a 4–20% SDS-PAGE gel and run under reducing conditions. After electrophoresis, the proteins on the gel were transferred to PVDF membrane and blocked with 5% dry milk in 20 mM Tris-buffered saline with 0.05% TWEEN®-20 surfactant. The membranes were incubated overnight at 4° C. with 1:1000 dilution of rabbit polyclonal anti-CR-1 antibody (Biocon). One membrane was probed with 1:1000 dilution of rabbit polygonal anti-CR-1 antibody that had been preincubated with human recombinant CR-1 (1 μg/ml) for 2 hr at room temperature. The bound rabbit antibody was detected using 1:2000 dilution of a goat anti-rabbit IgG conjugated to horseradish peroxidase (Amersham) and immunoreactive bands were detected by enhanced chemiluminescence (Amersham).

As shown in FIG. 1, a band of 28 kDa reacting with the rabbit polyclonal anti-CR-1 antibody was identified at varying intensity in the human milk samples. All of the samples tested expressed immunoreactive CR-1 protein but to various degrees.

To demonstrate that the band recognized by the anti-CR-1 antibody is specific, samples 1 to 9 were probed with the rabbit polyclonal anti-CR-1 antibody that had been preincubated with an excess of recombinant CR-1. No bands were detected when the samples were incubated with the anti CR-1 antibody preabsorbed with the CR-1 protein, demonstrating the specificity of the band that was recognized by the anti-CR-1 antibody (FIG. 2). The presence and amount of CR-1 in human milk was also assessed and quantified by ELISA, as described below in Example 2.

EXAMPLE 2

Enzyme-Linked Immunosorbent Assay (ELISA)

In these experiments, 200 µl of each delipidated milk sample were added to 96 microtiter well plates and incubated overnight at 4° C. Human recombinant CR-1 protein was also absorbed at concentrations ranging from 100 pg to 1 µg. The plates were blocked with 2% milk (Kirkergaard & Perry) for 1 hr at 37° C. and incubated with 1:3000 dilution of rabbit polyclonal anti-CR-1 antibody (Biocon) for 1 hr at 37° C. After washing the plates 3 times with washing buffer (Kirkergaard & Perry), 1:3000 dilution of donkey anti-rabbit IgG conjugated to horseradish peroxidase (Amersham) was added and incubated for 1 hr at 37° C. The plates were then washed five times with washing buffer and 100 µl of TMB peroxidase substrate buffer (Kirkergaard & Perry) were added to the wells. To allow for color development, the plates were incubated in the dark for 5 min. The reaction was stopped by the addition of stop solution (Kirkergaard & Perry) and the absorbance was read at 450 nm. The experiment was performed in triplicate and repeated three times.

Results of some ELISA experiments are shown in FIG. 3. FIG. 3, Panel A provides results for plates in which the concentration of CR-1 in the samples was estimated using different concentrations of recombinant CR-1 protein. This Figure shows that the rabbit anti-CR-1 polyclonal antibody can linearly detect recombinant human CR-1 over a concentration range of 100 pg to 1 µg. In addition, as indicated in FIG. 3, Panel B, immunoreactive CR-1 was present at concentrations from 62 to 118 ng/ml in the milk samples. There was a significant correlation between the relative amounts of the 28 kDa CR-1 immunoreactive protein in the milk samples as detected by Western blot analysis (as described in Example 1) and the concentration of immunoreactive CR-1 that was measured in the ELISA described in this Example.

EXAMPLE 3

Immun Purification of CR-1 Protein from Human Milk

CR-1 protein from human milk was purified using an AMINOLINK® Plus immobilization kit (Pierce), as per the manufacturer's instructions. Briefly, rabbit polyclonal anti-CR-1 IgG was coupled to AMINOLINK® Plus coupling gel using a pH 10 coupling buffer containing 0.1 M sodium citrate and 0.05 M sodium carbonate. The anti-CR-1 antibody-coupled column was then used for affinity purification of CR-1 from delipidated human milk. Human milk sample number 2, because of its high CR-1 levels as detected by Western blot (See Example 1) and by ELISA (See, Example 2), was chosen for purification.

Figure 4:
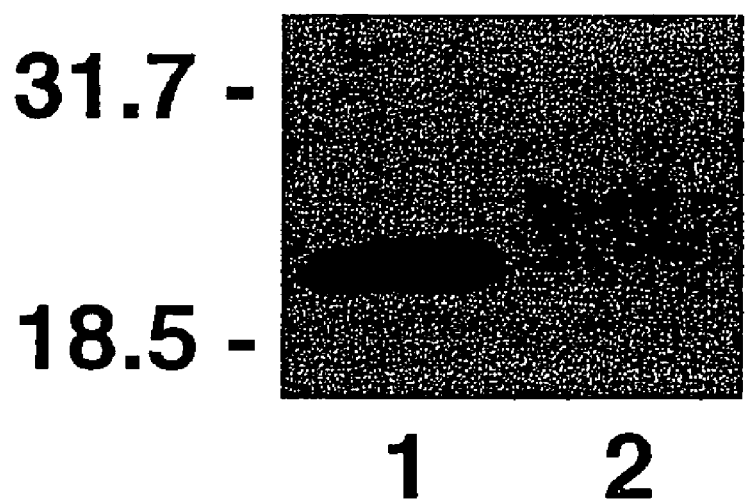
FIG. 4 provides results for Western blot analyses of immunopurified milk-derived CR-1, probed with rabbit polyclonal anti-CR-1 antibody. In this experiment, 100 ng of human recombinant CR-1 protein (lane 1) and 40 µl of the immunopurified milk sample (lane 2) were run on a 4–20% SDS-PAGE gel and following transfer for Western analysis, the samples were probed with 1:1000 dilution of rabbit polyclonal anti-CR-1 antibody.

Five ml of human milk were applied to the column and incubated for 1 hr at room temperature. After washing with PBS, the bound CR-1 protein was eluted in several fractions with 0.1 M glycine pH 2.5, and neutralized with 1 M Tris pH 9.5. The fractions containing the protein were pooled, concentrated with a CENTRICON® 10 (Amicon) concentrator and dialyzed against PBS. The concentration of the purified protein was estimated by Western blot using known concentrations of recombinant human CR-1 as a reference, as described in Example 1. In this Western blot, 100 ng of human recombinant CR-1 protein (lane 1) and 40 µl of the immunopurified milk sample (lane 2) were run on a 4–20% SDS-PAGE gel and probed with 1:1000 dilution of rabbit polyclonal anti-CR-1 antibody. The results are shown in FIG. 4.

EXAMPLE 4

Bioassay of Milk-Derived CR-1 Protein

To test the activity of purified CR-1 protein from human milk, NMuMG mouse mammary epithelial cells were seeded in 100 mm plates and were grown until they reached 70–80% confluence. The cells were then switched to serum-free Dulbecco's modified Eagle's medium containing human transferrin (10 µg/ml) and type IV Pedersen fetuin (1 mg/ml) for 24 hr. Cells were stimulated for 5 min at 37° C. with recombinant human CR-1 protein at 100 ng/ml or CR-1 that was purified from human milk by immunoaffinity chromatography as described in Example 2). The cells were lysed in a buffer containing 20 mM Tris-HCl, pH 7.5, 150 mM NaCl, 1% Nonidet P-40, 0.5% deoxycholate, 5 mM $MgCl_2$, 2 µg/ml aprotinin, 2 µg/ml leupeptin, 1 mM phenylmethylsulfonyl fluoride, 1 mM sodium orthovanadate, and 20 mM sodium fluoride.

Crude protein lysates (30 µg/sample) were run on a 10% SDS-PAGE gel, transferred to PVDF membrane, blocked in a solution prepared from 5% dry milk (See, Example 1) and incubated with a 1:1000 dilution of a rabbit polyclonal anti-phospho MAPK antibody (Biolab). After incubation with a goat anti-rabbit IgG conjugated to horseradish peroxidase (Amersham), the immunoreactive bands were detected by enhanced chemiluminescence (Amersham).

Figure 5:
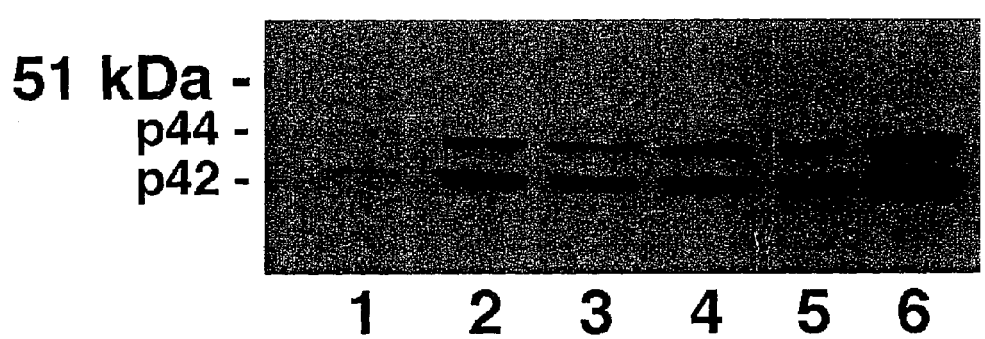
FIG. 5 provides SDS-PAGE results of experiments involving MAPK phosphorylation in NMuMG mouse mammary epithelial cells induced by CR-1 purified from human milk. Serum-starved NMuMG cells were stimulated for 5 minutes at 37° C., with different concentrations of CR-1 that had been immunopurified from human milk at various concentrations. Cell lysates were run on a 10% SDS-PAGE gel. Following transfer for Western analysis, the samples were probed with an anti-phospho MAPK rabbit polyclonal antibody (Biolab) that recognizes the activated phosphorylated forms of MAPK (p44 and p42). Lane 1 contains serum-starved cells; lane 2 contains rhCR-1, 100 ng/ml; lane 3 contains milk CR-1 50 ng/ml; lane 4 contains milk CR-1 100 ng/ml; lane 5 contains milk CR-1 300 ng/ml; and lane 6 contains milk CR-1 500 ng/ml.

FIG. 5 provides results for cell lysates were run on a 10% SDS-PAGE gel and probed with an anti-phospho MAPK rabbit polyclonal antibody (Biolab) that recognizes the activated phosphorylated forms of MAPK (p44 and p42). In this Figure, Lane 1 contains serum-starved cells; lane 2 contains rhCR-1 (100 ng/ml); lane 3 contains milk CR-1 (50 ng/ml); lane 4 contains milk CR-1 (100 ng/ml); lane 5 contains milk CR-1 (300 ng/ml); and lane 6 contains milk CR-1 (500 ng/ml).

As indicated in FIG. 5, a dose-dependent activation of MAPK was detected following treatment of the cells with milk-derived CR-1. Recombinant human CR-1 (100 ng/ml) was also able to stimulate MAPK phosphorylation at a level that was nearly equivalent to the level of MAPK stimulation by 100 ng/ml of milk-derived CR-1.

EXAMPLE 5

Detection of Cripto-1 in Human Plasma

Figure 6:
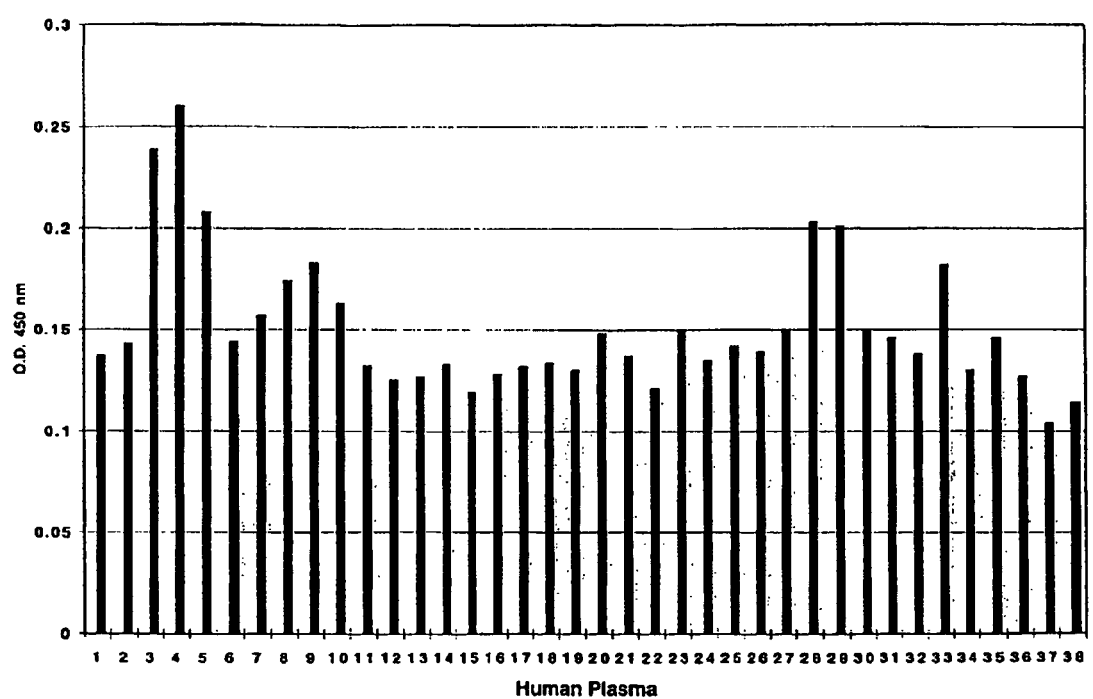
FIG. 6 provides a graph showing the $OD_{450}$ results for 28 human plasma samples, indicating the presence of CR-1 in varying concentrations in these samples.

In these experiments, 200 µl aliquots from human plasma samples obtained from 38 breast cancer patients were added to 96 microtiter well plates and incubated overnight at 4° C. Human recombinant CR-1 protein was also absorbed at concentrations ranging from 100 pg to 1 µg. The plates were blocked with 2% milk solution (Kirkergaard & Perry) for 1 hr at 37° C., and incubated with 1:3000 dilution of rabbit polyclonal anti-CR-1 antibody (Biocon) for 1 hr at 37° C. After washing the plates 3 times with washing buffer (Kirkergaard & Perry), 1:3000 dilution of donkey anti-rabbit IgG conjugated to horseradish peroxidase (Amersham) was added for 1 hr at 37° C. The plates were then washed five times with washing buffer and 100 µl of TMB peroxidase substrate buffer (Kirkergaard & Perry) was added to the wells. To allow for color development, the plates were incubated in the dark for 5 min. The reaction was stopped by the addition of stop solution (Kirkergaard & Perry) and the absorbance was read at 450 nm. The experiment was performed in triplicate and repeated three times. Results of these ELISA experiments are shown in FIG. 6. As indicated in this Figure, CR-1 was present in these samples at varying concentrations.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of immunoassays, molecular biology, endocrinology, and/or related fields are intended to be within the scope of the present invention.

We claim:

1. A method for detection of Cripto-1 in a sample of bodily fluid, comprising:
    a) providing:
        i) a sample of bodily fluid suspected of containing Cripto-1,
        ii) an antibody directed against said Cripto-1;
    b) exposing the bodily fluid sample to the antibody under conditions such that Cripto-1 and the antibody bind to form an antigen-antibody complex; and
    c) detecting the antigen-antibody complex.

2. The method of claim 1, wherein the bodily fluid sample is milk.

3. The method of claim 1, wherein the bodily fluid sample is from a human.

4. The method of claim 1, wherein the antibody is a monoclonal antibody.

5. The method of claim 1, wherein the method comprises the use of an enzyme-linked immunosorbent assay.

6. The method of claim 1, further comprising a step of quantitating Cripto-1 in the bodily fluid sample.

7. A method for quantitating Cripto-1 in a sample of bodily fluid, comprising:
    a) providing:
        i) a sample of bodily fluid containing Cripto-1,
        ii) an antibody directed against Cripto-1;
    b) exposing the bodily fluid sample to the antibody under conditions such that said Cripto-1 and antibody bind to form an antigen-antibody complex; and
    c) measuring the amount of the antigen-antibody complex.

8. The method of claim 7, wherein the bodily fluid sample is milk.

9. The method of claim 7, wherein the bodily fluid sample is from a human.

10. The method of claim 7, wherein the antibody is a monoclonal antibody.

11. The method of claim 7, wherein the method comprises the use of an enzyme-linked immunosorbent assay.

12. A method for detecting and quantitating Cripto-1 in a sample of bodily fluid, comprising:
    a) providing:
        i) a sample of bodily fluid suspected of containing Cripto-1,
        ii) an antibody directed against Cripto-1;
    b) exposing the bodily fluid sample to the antibody under conditions such that Cripto-1 and antibody bind to form an antigen-antibody complex;
    c) detecting the antigen-antibody complex; and
    d) measuring the amount of the antigen-antibody complex.

13. The method of claim 12, wherein the bodily fluid sample is milk.

14. The method of claim 12, wherein the bodily fluid sample is from a human.

15. The method of claim 12, wherein the antibody is a monoclonal antibody.

16. The method of claim 12, wherein the method comprises the use of an enzyme-linked immunosorbent assay method.

17. The method of claim 1, wherein the bodily fluid sample is serum.

18. The method of claim 1, wherein the antibody is a polyclonal antibody.

19. The method of claim 7, wherein the bodily fluid sample is serum.

20. The method of claim 7, wherein the antibody is a polyclonal antibody.

21. The method of claim 12, wherein the bodily fluid sample is serum.

22. The method of claim 12, wherein the antibody is a polyclonal antibody.

23. The method of claim 1, wherein the bodily fluid sample is plasma.

24. The method of claim 7, wherein the bodily fluid sample is plasma.

25. The method of claim 12, wherein the bodily fluid sample is plasma.

* * * * *